United States Patent
Kantor (10) Patent No.: US 8,001,925 B2
(45) Date of Patent: Aug. 23, 2011

(54) DRUG-POLYMER COATED STENT

(75) Inventor: John Kantor, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 12/719,699

(22) Filed: Mar. 8, 2010

(65) Prior Publication Data

US 2010/0174353 A1    Jul. 8, 2010

Related U.S. Application Data (62) Division of application No. 11/568,788, filed as application No. PCT/US2005/015622 on May 4, 2005, now Pat. No. 7,704,545.

(60) Provisional application No. 60/570,237, filed on May 12, 2004.

(51) Int. Cl.
*B05C 13/00* (2006.01)

(52) U.S. Cl. ............... 118/500; 623/1; 623/11; 118/200; 118/209

(58) Field of Classification Search ............... 623/1, 11; 118/500

See application file for complete search history.

(56) References Cited

U.S. PATENT DOCUMENTS

| | | | |
|---|---|---|---|
| 4,212,304 A | | 7/1980 | Finney |
| 5,423,885 A | * | 6/1995 | Williams ............. 623/1.17 |
| 6,004,348 A | * | 12/1999 | Banas et al. ............. 623/23.7 |

FOREIGN PATENT DOCUMENTS

| | | | |
|---|---|---|---|
| WO | WO00/12147 | | 3/2000 |
| WO | WO 00/12147 | * | 3/2000 |
| WO | WO03/005990 | | 1/2003 |

* cited by examiner

*Primary Examiner* — Dah-Wei Yuan
*Assistant Examiner* — Andrew Bowman (57) ABSTRACT

The present invention provides a method and system for loading drug onto a stent. The method comprises positioning at least one polymer coated stent on a mandrel, positioning a drug infused sheath onto the stent and diffusing drug from the sheath into the polymer coating of the stent. The system includes a drug coated mandrel and sheath positioned adjacent to and in contact with a polymer coated stent.

9 Claims, 5 Drawing Sheets

DRUG-POLYMER COATED STENT

RELATED APPLICATIONS

This application is a Division of and claims the benefit of U.S. patent application Ser. No. 11/568,788 filed Nov. 7, 2006 which claims priority from National Stage PCT/US2005/015622 filed May 4, 2005 which claims priority from U.S. Provisional Application No. 60/570,237 filed May 12, 2004, the disclosures of which are herein incorporated by reference in their entirety.

FIELD OF THE INVENTION

This invention relates generally to biomedical stents. More specifically, the invention relates to a drug-polymer coating disposed on an endovascular stent for in vivo, drug delivery, and methods of coating thereof.

BACKGROUND OF THE INVENTION

Endovascular stents have become increasingly important in medical procedures to restore the function of bodily lumens. With generally open tubular structures, the stents typically have apertured or lattice-like walls of a metallic or polymeric base, and can be either balloon expandable or self-expanding. A stent is typically deployed by mounting the stent on a balloon portion of a balloon catheter, positioning the stent in a body lumen, and expanding the stent by inflating the balloon. The balloon is then deflated and removed, leaving the stent in place. Stents help reduce the probability and degree of vessel blockage from restenosis.

An increasing number of stents for treating vascular conditions are being coated with protective materials and bioactive drugs. A variety of stent coatings and compositions have been proposed to provide localized therapeutic pharmacological agents and treatment of a vessel at the site being supported by the stent. Stent coatings with various families of drug polymer chemistries have been used to increase the effectiveness of stenting procedures and to control drug-elution properties. For example, polymeric coatings can be made from polyurethane, polyester, polylactic acid, polyamino acid, polyorthoester, and polyphosphate ester. Examples of drug or bioactive agents include antirestonotic and anti-inflammatory compounds.

Medical research indicates a greater effectiveness of vascular stents when stents are coated with pharmaceutical drugs that help prevent or treat medical conditions such as restenosis and thrombosis. These drugs may be released from a coating while in the body, delivering their patent effects at the site where they are most needed. The localized levels of the medications can be elevated, and are therefore potentially more effective than orally or intravenously delivered drugs. Furthermore, drugs released from tailored stent coatings can have controlled, timed-release qualities, eluting their bioactive agents over hours, weeks or even months. Stent coatings typically have a drug or active agent, which has been dissolved or dispersed throughout the polymeric material and physically constrained within the polymer. The sustained release of drugs generally relies upon either degradation of the polymer or diffusion through the polymer to control the elution of the compounds.

Stents can be coated with a polymer or combination of a polymer and a pharmaceutical agent or drug by application techniques such as dipping, spraying, painting, and brushing. In many of the current medical device or stent coating methods, a composition of a drug and a polymer in a solvent is applied to a device to form a substantially uniform layer of drug and polymer. The concentration of the pharmaceutical agent or drug applied to the stent varies depending on the pharmaceutical agent or drug and the intended use of the pharmaceutical agent or drug. Generally, the dose of pharmaceutical agent or drug coated on a stent ranges from nanograms to milligrams. A problem arises when trying to coat stents with lower doses of pharmaceutical agent or drug.

A common solvent for the polymers and drugs employed is usually required, and techniques have been developed to micronize the drugs into small particles so that the drugs can be suspended in the polymer solution. Micronization can be time consuming, and may result in a degradation or loss of desired therapeutic properties of the drug. A method of using micronized drugs and layering a drug-coated stent using pharmacological and polymeric agents is described by Guruwaiya et al. in U.S. Pat. No. 6,251,136 issued Jun. 26, 2001. A pharmacological agent is applied to a stent in dry, micronized form over a sticky base coating. A membrane-forming polymer, selected for its ability to allow the diffusion of the pharmacological agent therethrough, is applied over the entire stent. More specifically, a stent, typically a metal stent, has a layer of a sticky material applied to selected surfaces of the stent. A pharmacological agent is layered on the sticky material and a membrane forming a polymer coating is applied over the pharmacological agent. The membrane is formed from a polymer that permits diffusion of the pharmacological agent over a predetermined time period.

A method of applying drug-release polymer coatings that uses solvents is described in "Method of Applying Drug-Release Coatings", Ding et al., U.S. Pat. No. 5,980,972 issued Nov. 9, 1999. A polymer is dissolved in one solvent and a drug is dissolved or suspended in a similar or different type of solvent. The solutions are applied either sequentially or simultaneously onto the devices by spraying or dipping to form a substantially homogenous composite layer of the polymer and the biologically active material.

Many of the drug-coated stents in recent years have been sprayed with rather than dipped in a drug-polymer solution. Spray coating, a currently preferred method for coating stents, can result in a significant amount of spray material lost during the process and when expensive drugs are used in these coatings, the use of spray coating may be costly. Another drawback to spraying is that spraying deposits an inexact amount of therapeutic agent on the stent, potentially delivering more or less than desired. This is a problem where the therapy requires a more controlled amount of drug be administered to the target site. This is also a problem where a very small concentration of therapeutic agent is to be applied to and eluted from the stent.

Dip coating was used with early stents and other medical-device designs that were of relatively open construction fabricated from wires or from ribbons. Such coating methods were performed by manually dipping the stent in a liquid, and then removing the stent and drying it. The dipping process requires care to avoid excess liquid on the stent framework or inconsistent drying of the liquid, otherwise the apertures can become blocked unnecessarily. Applying a thick coating tends to exacerbate webbing and bridging problems, and increasing the solids content of the coating solution also increases webbing and bridging between the struts. Any coating method needs to avoid webbing, as well as control the weight and thickness of a coating.

Newer stents that are of less open construction, such as catheter-deployed, self-expanding stents are more difficult to coat evenly using a dipping method. Nevertheless, one advantage of dip coating is the ability to process a greater number of stents in a more efficient manufacturing process.

Dipping as a method of coating medical devices is described in U.S. Patent Application No. 20020082679 published Jun. 27, 2002 entitled "Delivery or Therapeutic Capable Agents" to Sirhan and Yan. Barry et al. describe another method of dip coating a stent with a polymer composition that can be used for delivering substantially water-insoluble drugs in "Loading and Release of Water-Insoluble Drugs", U.S. Pat. No. 6,306,166 issued Oct. 23, 2001.

Multiple dips can be used to build up the weight and thickness of the coating, but each subsequent dip may affect the coating already deposited. A coating can re-dissolve in a second coating solution, causing some loss of the first layer of coating. Also, applications of multiple dip coats from low concentration solutions can have the effect of reaching a limiting loading level as equilibrium is reached between the solution concentration and the amount of coating with or without a pharmaceutical agent. One such method that applies a plurality of relatively thin coatings on an open-lattice stent is disclosed in "Drug Release Stent Coating", Ding et al., U.S. Pat. No. 6,358,556 issued Mar. 19, 2002. The stents are coated by dipping or, preferably, spraying the stent with a solvent mixture of uncured polymeric silicone material with a cross-linker and a finely divided biologically active species.

Accordingly, what is needed is a method for coating medical devices such as stents with drug-polymer coating with more accuracy than current methods of coating and that overcomes the deficiencies and limitations described above.

SUMMARY OF THE INVENTION

One aspect of the invention provides a method of loading drug onto a stent. The method comprises positioning at least one polymer coated stent on a mandrel, positioning a drug infused sheath onto the stent and diffusing drug from the sheath into the polymer coating of the stent.

Another aspect of the invention provides a system for loading drug onto a stent. The system comprises a polymer coated stent and a stent holding member. The stent holding member is sized to receive the polymer coated stent. The system further includes a drug-coated sheath sized to fit around the stent and mandrel during diffusion of the drug into the polymer coating on the stent.

Another aspect of the invention is a method of treating a vascular condition. The method includes the steps of inserting a drug-polymer coated stent within a vessel of a body, the drug-polymer coated stent including a drug-polymer coating having at least one therapeutic agent and eluting at least one therapeutic agent from the laminated drug-polymer coating into the body.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

DETAILED DESCRIPTION OF THE PRESENTLY PREFERRED EMBODIMENTS

Figure 1:
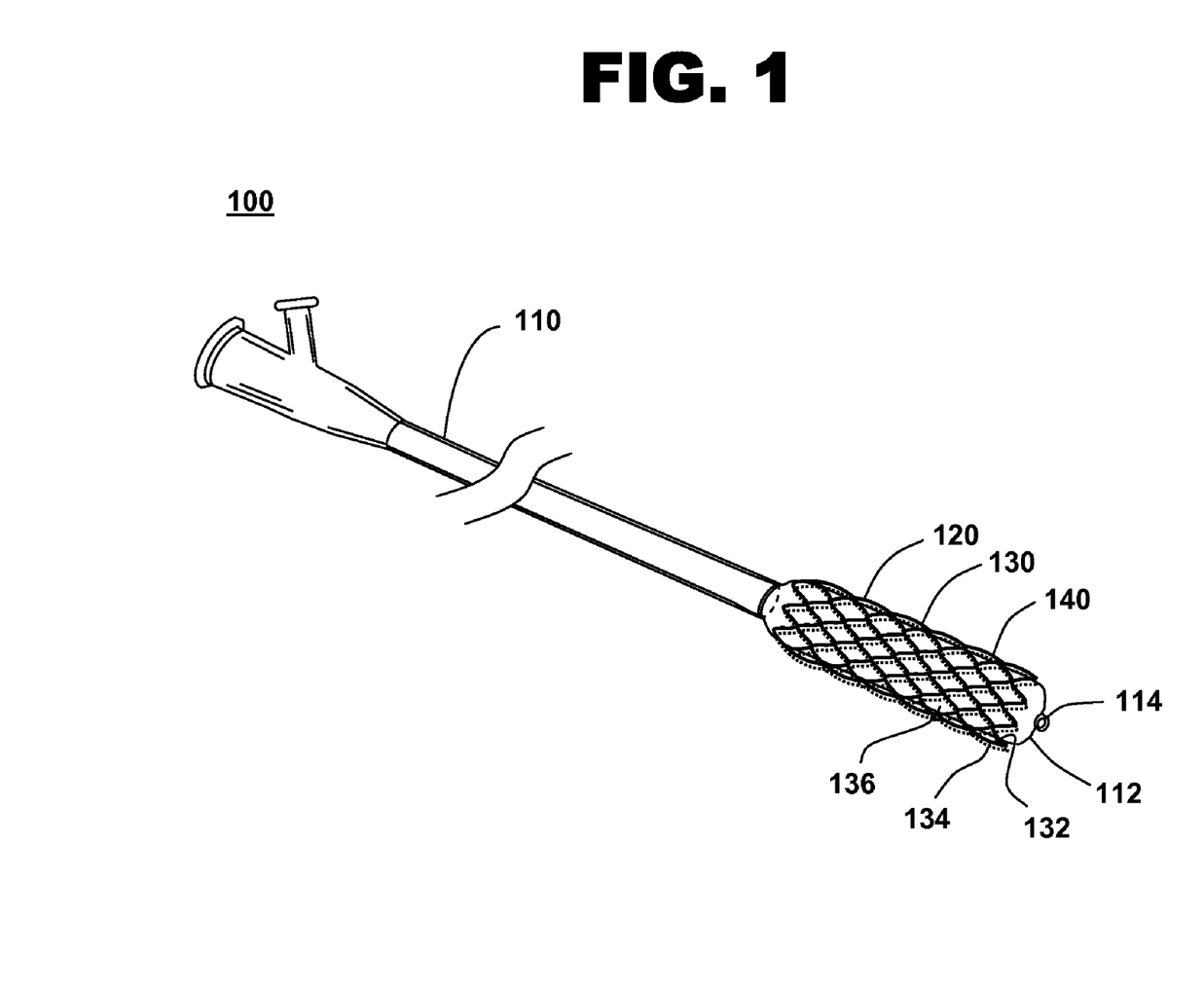
FIG. 1 is an illustration of a system for treating a vascular condition including a drug-polymer coated stent coupled to a catheter, in accordance with one embodiment of the current invention.

FIG. 1 shows an illustration of a system for treating a vascular condition, comprising a drug-polymer coated stent coupled to a catheter, in accordance with one embodiment of the present invention at 100. Coated stent with catheter 100 includes a drug-polymer coated stent 120 coupled to a delivery catheter 110. Drug-polymer coated stent 120 includes a stent framework 130 and a drug-polymer coating 140 disposed on stent framework 130. Drug-polymer coating 140 is applied to at least a portion of the stent framework, such as an inner surface 132 of stent framework 130, an outer surface 134 of stent framework 130, or both inner surface 132 and outer surface 134 of stent framework 130. In other embodiments, portions of the sent may be coated with a drug-polymer coating, leaving some of the stent uncoated. For example, only the ends of the stent may be coated or only the middle of the stent may be coated, leaving the ends uncoated. Drug-polymer coating 140 comprises a drug-polymer and at least one therapeutic agent.

Stent framework 130 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art.

Insertion of coated stent 120 into a vessel of a body helps treat, for example, heart disease, various cardiovascular ailments, and other vascular conditions. Catheter-deployed coated stent 120 typically is used to treat one or more blockages, occlusions, stenoses or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

An exemplary drug-polymer coating 140 includes or encapsulates one or more therapeutic agents. Drug-polymer coating 140 may comprise one or more therapeutic agents dispersed within or encased by drug-polymer layers on coated stent 120, which are eluted from coated stent 120 with controlled time delivery after the deployment of coated stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Drug-polymer coating 140 may comprise, for example, an antirestenotic drug such as rapamycin, a rapamycin analogue, or a rapamycin derivative to prevent or reduce the recurrence or narrowing and blockage of the bodily vessel. Drug-polymer coating 140 may comprise an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof.

The elution rates of the therapeutic agents and total drug eluted into the body and the tissue bed surrounding the stent framework are based on the thickness of drug-polymer coating 140, the constituency of drug-polymer coating 140, the nature and concentration of the therapeutic agents, the thickness and composition of any cap coat, and other factors. Drug-polymer coating 140 may include and elute multiple therapeutic agents to achieve the desired therapeutic effect. Drug-polymer coating 140 can be tailored to control the elution of one or more therapeutic agents, primarily by diffusion processes. In some cases, a portion of drug-polymer coating 140 dissolves and is absorbed into the body, releasing therapeutic agents from within the coating as the therapeutic agents are exposed to the surrounding tissue bed or bodily fluids flowing through the coated stent. In other cases, drug-polymer coating 140 erodes from coated stent 120 to release the therapeutic compounds, the residual polymer being expelled by the body.

Incorporation of a drug or other therapeutic agent into drug-polymer coating 140 allows, for example, the rapid delivery of a pharmacologically active drug or bioactive agent within twenty-four hours following the deployment of a stent, with a slower, steady delivery of a second bioactive agent over the next three to six months. For example, a first therapeutic agent may comprise an antirestenotic drug such as rapamycin, a rapamycin analogue, or a rapamycin derivative. The second therapeutic agent may comprise, for example, an anti-cancer drug such as camptothecin or other topoisomerase inhibitors.

The amount of the therapeutic agent applied to the stent through the drug-polymer coating may vary depending on the characteristics of the particular agent or combination of agents, the length of time the stent is in place and other factors well known to those with skill in the art. In one embodiment, the drug or therapeutic agent is coated to achieve a total amount loaded on the stent to be between about 1 µg to about 10 µg. In another embodiment, the amount loaded onto the stent is between about 10 µg to about 1000 µg. Those with skill in the art will recognize that the method of loading the drug or therapeutic agent disclosed here allows for precise control of the amount loaded as well as allows for the loading of amounts below that allowed by current methods of application such as, for example, dipping, spraying and brushing.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a contrast fluid that fills a tube inside catheter 110 and balloon 112. Coated stent 120 is expanded until a desired diameter is reached, and then the fluid is depressurized or pumped out, separating balloon 112 from coated stent 120 and leaving coated stent 120 deployed in the vessel of the body. Alternatively, catheter 110 may include a sheath that retracts to allow expansion of a self-expanding version of coated stent 120.

Figure 2A:
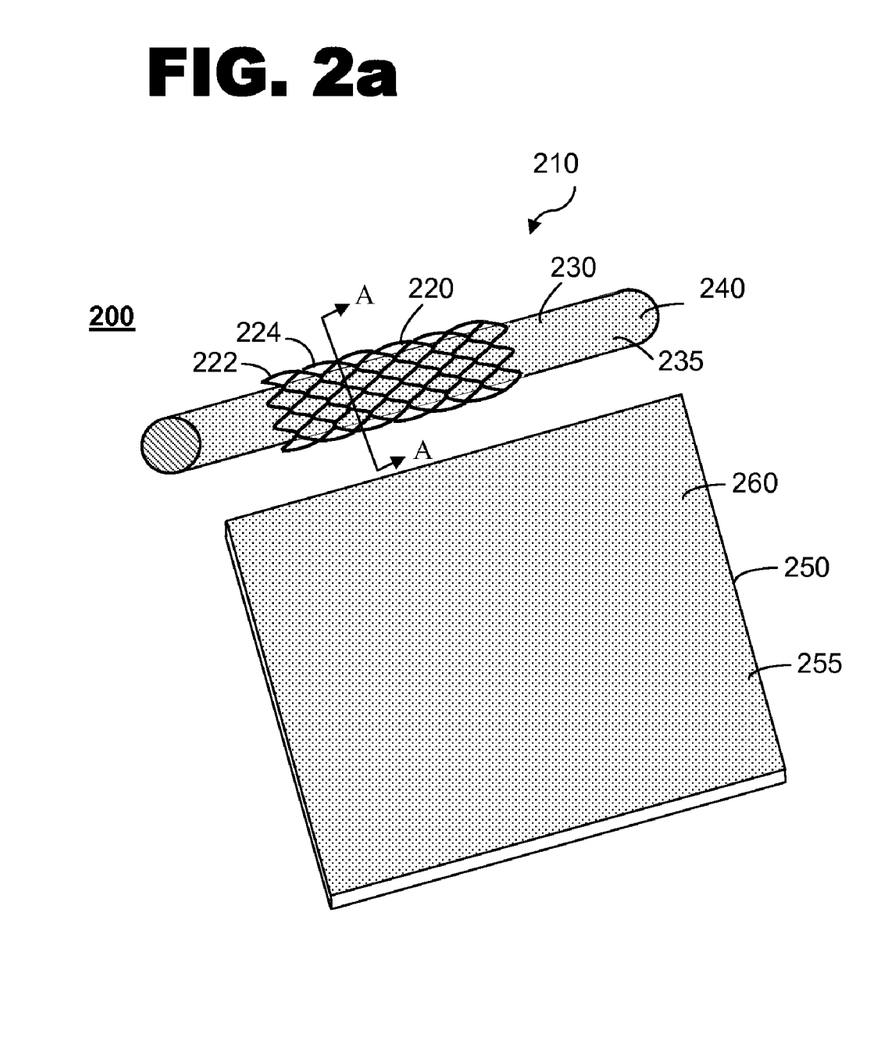
FIGS. 2a and 2b illustrate one embodiment of a system for applying a therapeutic agent to a polymer-coated stent, in accordance with one embodiment of the current invention.
Figure 2B:
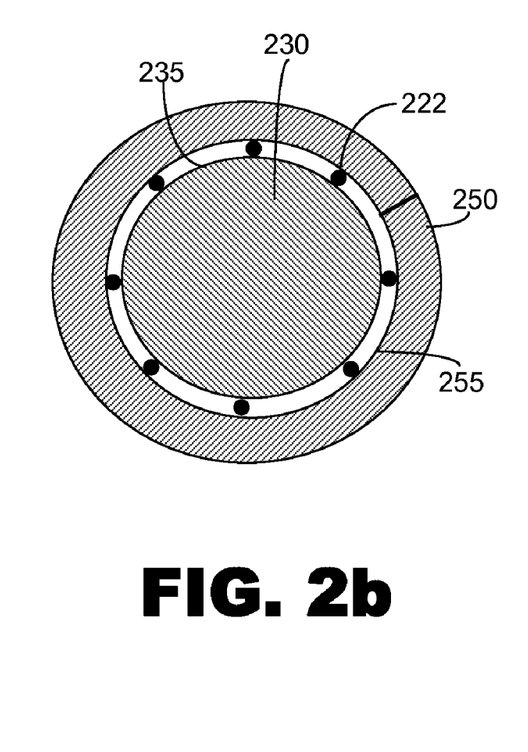

FIGS. 2a and 2b illustrate a system for applying a drug-polymer coating to a stent, in accordance with one embodiment of the present invention at 200. Stent coating system 200 provides a system for uniformly applying a therapeutic agent to both the inside and outside diameter of the stent. Coating system 200 includes a polymer-coated stent 220, stent holding member (mandrel) 230 and drug delivery sheath 250. Polymer coated stent 220 includes a stent framework 222 with a polymer coating 224 disposed on stent framework 222. Polymer coating 224 may be uniformly distributed around stent framework 222 thereby coating the entirety of stent 220. Polymer coating 224 may be any one or combination of polymers well known to those with skill in the art. Polymer coating 224 may be, for example, poly(ethylene-vinyl acetate) (PEVA), polyurethane, polycaprolactone, phosphoryl choline or a blended polymer of polyurethane and polycaprolactone.

Stent framework 222 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art.

Mandrel 230 is of a size and shape suitable to support a stent for coating. The stent may be coated in the fully deployed state, the rolled down state or a partially open state. Stent 220 is disposed around the mandrel adjacent to the outside surface 235 of mandrel 230. The outside surface 235 of mandrel 230 includes a drug-polymer coating 240. Drug-polymer coating 240 may comprise a drug or other therapeutic agent of the type described above for FIG. 1 or any other suitable agent well known in the art. Drug-polymer coating 240 may be applied to mandrel 230 by dipping, spraying, brushing or any other means known in the art.

Drug delivery sheath 250 includes a drug-polymer coating 260 applied to sheath surface 255. Drug delivery sheath 250 is composed of a flexible material suitable for wrapping around the stent mandrel assembly 210. In one embodiment, drug delivery sheath 250 is a polymer. The polymer may be, for example, poly(ethylene-vinyl acetate) (PEVA), polyurethane, polycaprolactone, phosphoryl choline, a blended polymer of polyurethane and polycaprolactone or any other polymer well known to those with skill in the art.

Drug-polymer coating 260 may comprise a drug or other therapeutic agent of the type described above for FIG. 1 or any other suitable agent well known in the art. Drug-polymer coating 260 may include the same drug and polymer combination as that of drug-polymer coating 240 coated on mandrel 230 or it may be a different drug or therapeutic agent. Drug-polymer coating 260 may be applied to drug delivery sheath 250 by dipping, spraying, brushing, or any other means known in the art. Alternatively, the drug polymer coating may be applied by the method according to the present invention and described in more detail below.

In operation, drug delivery sheath 250 is wrapped around stent mandrel assembly 210 so that the drug-coated surface 255 of sheath 250 contacts the polymer coated stent framework 222. In this position, the drug or therapeutic agent of drug-polymer coating 240 and drug-polymer coating 260 will be diffused (transferred) to the polymer-coated stent. The diffusion of the drug or therapeutic agent will continue until a state of equilibrium is reached or until the stent is removed from contact with the mandrel and sheath. FIG. 2b is a cross section of system 200 taken along line A-A after the sheath 250 is wrapped around stent mandrel assembly 210.

The time that it takes to reach equilibrium varies depending on factors such as concentration of the drug or therapeutic agent on the sheath and mandrel, thickness of the polymer coating on the stent, molecular weight of the drug or therapeutic agent, and size of the molecule of the drug or therapeutic agent. The rate at which equilibrium is reached also may depend on the specific characteristics of the polymer coating.

The rate of diffusion of the drug or therapeutic agent from the drug-polymer coatings of the mandrel and the sheath to the polymer coating on the stent may be enhanced by increasing the temperature at which the sheath covered stent is placed. The sheath-covered stent may be place in an oven at temperatures ranging from about room temperature to a temperature below that at which the drug or therapeutic agent degrades. Those with skill in the art will recognize that the upper temperature limit depends on the specific drug or therapeutic agent.

The rate of diffusion may also be affected by increasing the atmospheric pressure to which the sheath-covered stent is exposed. In one embodiment, the sheath-covered stent may be placed in a pressure chamber and the pressure adjusted to above atmospheric pressure. The pressure may be increased, for example from about 0 atmospheres to about 150 atmospheres.

The rate of diffusion may also be affected by placing the sheath-covered stent in a solvent. The solvent may aid in the diffusion by providing a more suitable environment for the drug or therapeutic agent to migrate between the sheath mandrel and the polymer-coated stent. The solvent may be organic or inorganic. Those with skill in the art will recognize that the choice of solvent will depend on the characteristics of the drug or therapeutic agent to be coated.

Once equilibrium between the drug-polymer coated stent and the sheath and mandrel has been reached or a specific time has elapsed, the sheath may be removed from the stent mandrel assembly and the stent removed from the mandrel.

A cap coating may be applied to the drug-polymer coated stent before or after it is removed from the mandrel 230. The cap coating is applied by using, for example, any suitable application technique such as dipping, spraying, brushing or painting. The cap coating provides a level of scratch and abrasion resistance during the handling of the coated stent, and can serve as a diffusion barrier that provides additional control over the elution of therapeutic agents from the drug-polymer coating after deployment of the stent within the body. The cap coating may be formed from polymers such as polycaprolactone, polyglycolide, poly(lactide-co-glycolide), a silicone-urethane copolymer, a polyurethane, or poly(ethylene-vinyl acetate). Multiple cap coats may be applied to achieve a thicker cap coating.

In another embodiment of system 200, the mandrel does not include a drug-polymer coating. This embodiment may be used for applying drug or therapeutic agent to only the outer diameter of the polymer coated stent.

Those with skill in the art will appreciate that the drug may be applied in such a manner as to have a higher concentration of the drug in the outer polymer layer of the coated stent and a lower concentration in the polymer layer closest to the stent framework. This may be accomplished as a factor of time and by not allowing equilibrium to be achieved. Applying the drug to the stent in this manner preferentially loads the drug at the outer diameter of the stent where it is most useful. A stent having such a coating may be useful for situations where a higher dose of drug or therapeutic agent is initially required and a lower does desired over time.

Those with skill in the art will also recognize that system 200 may be designed to coat more than one stent at a time. For example, the mandrel 230 may be appropriately sized to accommodate two or more stents 220 with a correspondingly sized sheath 250.

Figures 3A, 3B:
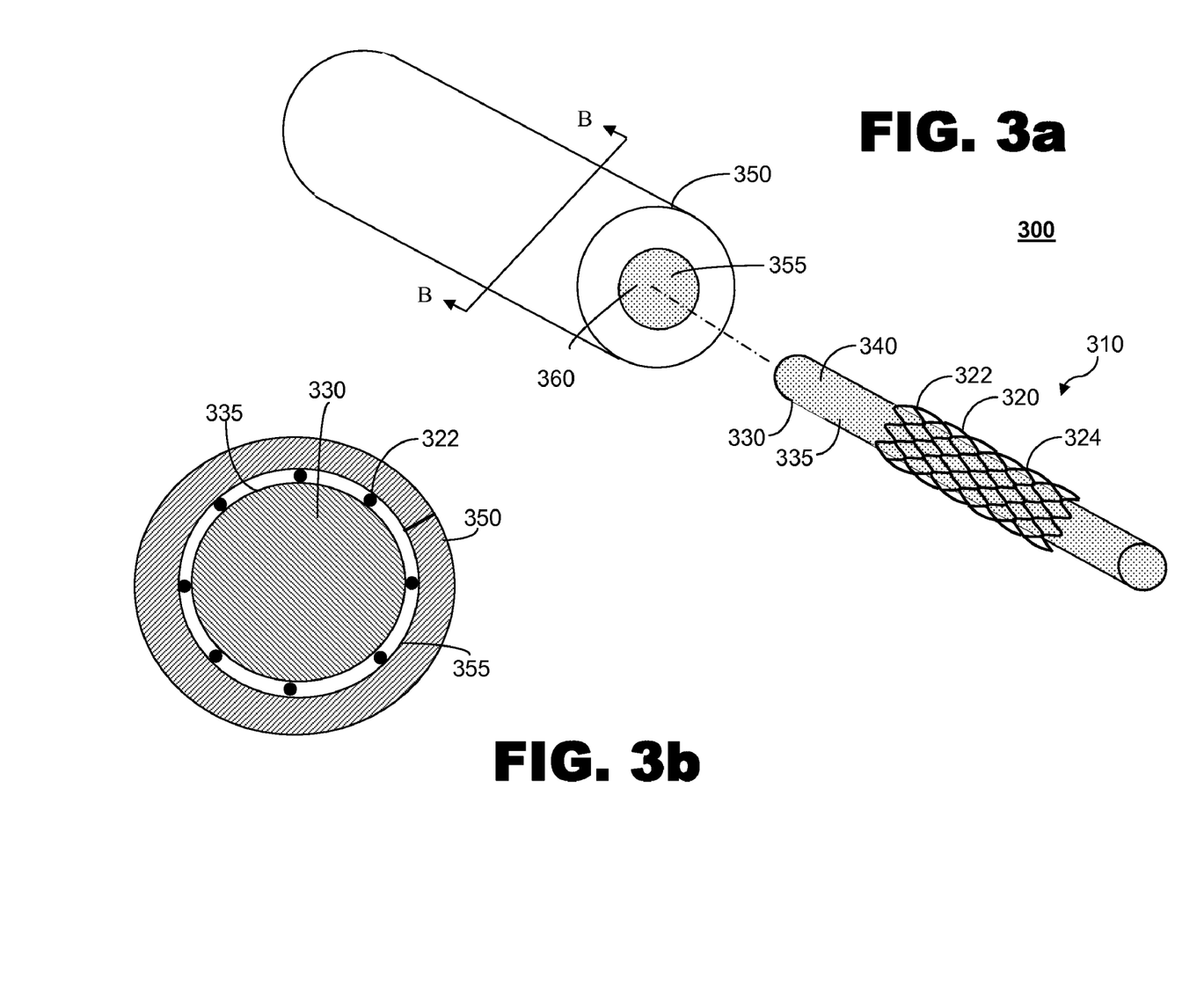
FIGS. 3a and 3b illustrate another embodiment of a system for applying a therapeutic agent to a polymer-coated stent, in accordance with one embodiment of the current invention.

FIGS. 3a and 3b illustrate a system for applying a drug-polymer coating to a stent, in accordance with another embodiment of the present invention at 300. Stent coating system 300 provides a system for uniformly applying a therapeutic agent to both the inside and outside diameter of the stent. Coating system 300 includes a polymer-coated stent 320, stent holding member (mandrel) 330 and drug delivery sheath 350. Polymer coated stent 320 includes a stent framework 322 with a polymer coating 324 disposed on stent framework 322. Polymer coating 324 may be uniformly distributed around stent framework 322 thereby coating the entirety of stent 320. Polymer coating 324 may be any one or combination of polymers well known to those with skill in the art. Polymer coating 324 may be, for example, poly(ethylene-vinyl acetate) (PEVA), polyurethane, polycaprolactone, phosphoryl choline or a blended polymer of polyurethane and polycaprolactone.

Stent framework 322 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art.

Those with skill in the art will recognize that stents composed of a polymer or a combination of polymers may not require that a polymer coating be applied prior to application of the drug or therapeutic agent to the stent.

Mandrel 330 is of a size and shape suitable to support a stent for coating. The stent may be coated in the fully deployed state, the rolled down state or a partially open state. Stent 320 is disposed around the mandrel adjacent to the outside surface 335 of mandrel 330. The outside surface 335 of mandrel 330 includes a drug-polymer coating 340. Drug-polymer coating 340 may comprise a drug or other therapeutic agent of the type described above for FIG. 1 or any other suitable agent well known in the art. Drug-polymer coating 340 may be applied to mandrel 330 by dipping, spraying, brushing or any other means known in the art.

Drug delivery sheath 350 includes a drug-polymer coating 360 applied to inner sheath surface 355. Drug delivery sheath 350 is composed of a flexible material suitable for placing around the stent mandrel assembly 310. In one embodiment, drug delivery sheath 350 is a polymer. The polymer may be, for example, poly(ethylene-vinyl acetate) (PEVA), polyurethane, polycaprolactone, phosphoryl choline, a blended polymer of polyurethane and polycaprolactone or any other polymer well known to those with skill in the art.

Drug-polymer coating 360 may comprise a drug or other therapeutic agent of the type described above for FIG. 1 or any other suitable agent well known in the art. Drug-polymer coating 360 may include the same drug and polymer combination as that of drug-polymer coating 340 coated on mandrel 330 or it may be a different drug or therapeutic agent. Drug-polymer coating 360 may be applied to the inside surface 355 drug delivery sheath 350 by dipping, spraying, brushing or any other means known in the art.

In operation, drug delivery sheath 350 is placed around stent mandrel assembly 310 so that the drug-coated surface 355 of sheath 350 contacts the polymer coated stent framework 322. The sheath may be composed of material that offers a degree of elasticity so that the sheath can be placed around and in contact with stent-mandrel assembly 310. In this position, the drug or therapeutic agent of drug-polymer coating 340 and drug-polymer coating 360 will be transferred (diffused) to the polymer-coated stent. The diffusion of the drug or therapeutic agent will continue until a state of equilibrium is reached or until the stent is removed from contact with the mandrel and sheath. FIG. 3b is a cross section of system 300 taken along line B-B after the sheath 350 is placed around stent mandrel assembly 310.

The time that it takes to reach equilibrium varies depending an factors such as concentration of the drug or therapeutic agent on the sheath and mandrel, thickness of the polymer coating on the stent, molecular weight of the drug or therapeutic agent, and size of the molecule of the drug or therapeutic agent. The rate at which equilibrium is reached also may depend on the specific characteristics of the polymer coating.

The rate of diffusion of the drug or therapeutic agent from the drug-polymer coatings of the mandrel and the sheath to the polymer coating on the stent may be enhanced by increasing the temperature at which the sheath covered stent is placed. The sheath-covered stent may be placed in an oven at temperatures ranging from about room temperature to a temperature below that at which the drug or therapeutic agent degrades. Generally, the temperature range at which the sheath-covered stent may be placed is between about 20 degrees Celsius to about 100 degrees Celsius. Those with skill in the art will recognize that the upper temperature limit depends on the specific drug or therapeutic agent.

The rate of diffusion may also be affected by increasing the atmospheric pressure to which the sheath-covered stent is exposed. In one embodiment, the sheath covered stent may be placed in a pressure chamber and the pressure adjusted to above atmospheric pressure. The pressure may be increased, for example from about 0 atmospheres to about 150 atmospheres.

The rate of diffusion may also be affected by placing the sheath-covered stent in a solvent. The solvent may aid in the diffusion by providing a more suitable environment for the drug or therapeutic agent to migrate between the sheath mandrel and the polymer-coated stent. The solvent may be organic or inorganic. Those with skill in the art will recognize that the choice of solvent will depend on the characteristics of the drug or therapeutic agent to be coated.

Once equilibrium between the drug-polymer coated stent 322 and the sheath and mandrel has been reached or a specific time has elapsed, the sheath 350 may be removed from the stent mandrel assembly and the stent removed from the mandrel. The sheath may be removed by cutting the sheath from the stent-mandrel assembly or in any other way so as not to damage the drug-polymer coating on stent 322. In another embodiment, the sheath is pressurized in order to expand the sheath sufficiently to aid its removal from the stent-mandrel assembly.

A cap coating may be applied to the drug-polymer coated stent before or after it is removed from the mandrel 330. The cap coating is applied by using, for example, any suitable application technique such as dipping, spraying, brushing or painting. The cap coating provides a level of scratch and abrasion resistance during the handling of the coated stent, and can serve as a diffusion barrier that provides additional control over the elution of therapeutic agents from the drug-polymer coating after deployment of the stent within the body. The cap coating may be formed from polymers such as polycaprolactone, polyglycolide, poly(lactide-co-glycolide), a silicone-urethane copolymer, a polyurethane, or poly(ethylene-vinyl acetate). Multiple cap coats may be applied to achieve a thicker cap coating.

In another embodiment of system 300, the mandrel does not include a drug-polymer coating. This embodiment may be used for applying drug or therapeutic agent to only the outer diameter of the polymer coated stent.

Those with skill in the art will appreciate that the drug may be applied in such a manner as to have a higher concentration of the drug in the outer polymer layer of the coated stent and a lower concentration in the polymer layer closest to the stent framework. This may be accomplished as a factor of time and by not allowing equilibrium to be achieved. A stent having such a coating may be useful for situations where a higher dose of drug or therapeutic agent is initially required and a lower does desired over time.

Those with skill in the art will also recognize that system 300 may be designed to coat more than one stent at a time. For example, the mandrel 330 may be appropriately sized to accommodate two or more stents 320 with a correspondingly sized sheath 350.

In another embodiment, the drug coated mandrel is not used to support the stent. In this embodiment, a self expanding polymer coated stent is placed within the sheath and allowed to expand to a point where the polymer coating of the stent framework is adjacent to and in contact with the drug-polymer coating on the inside surface of the drug delivery sheath. The stent is kept in an expanded state within the sheath until that time that equilibrium is reached or a predetermined amount of time has elapsed.

Figure 4:
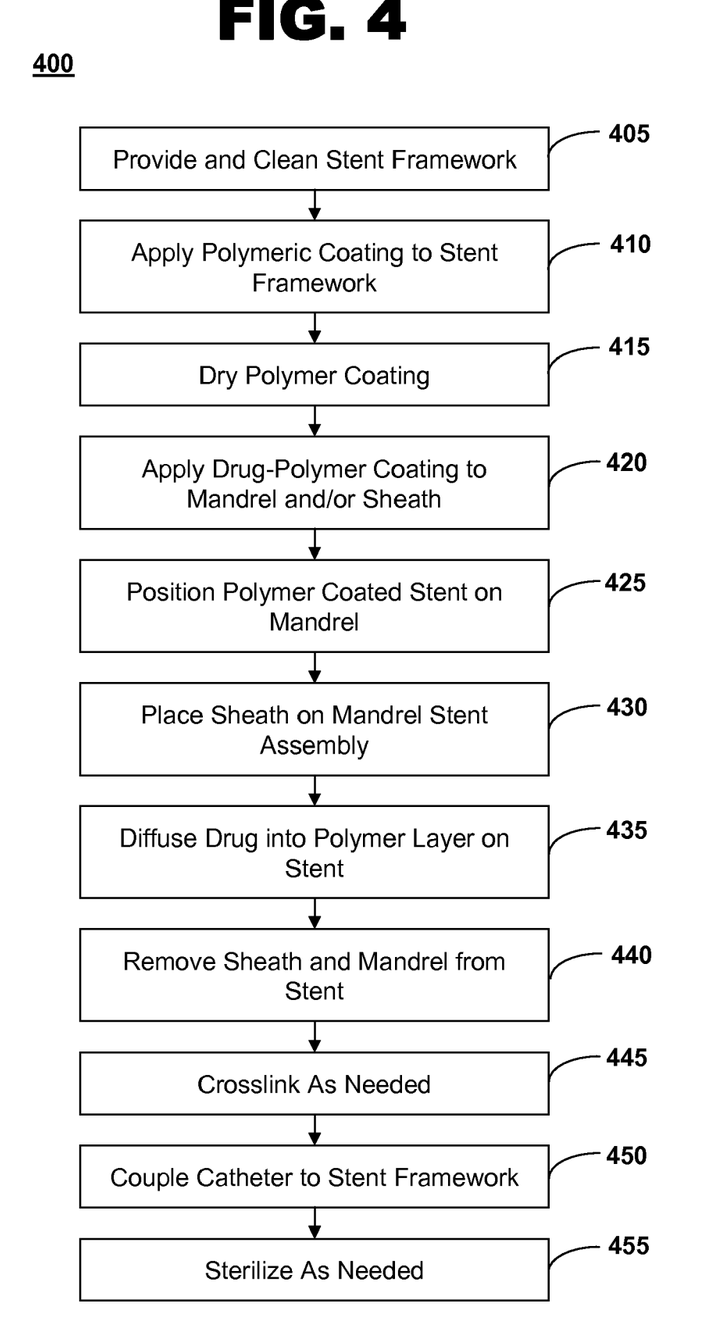
FIG. 4 is a flow diagram of a method of applying a therapeutic agent on a polymer coated stent, in accordance with one embodiment of the current invention.

FIG. 4 shows a flow diagram of a method of applying a drug-polymer coating on a stent, in accordance with one embodiment of the present invention at 400. Drug-polymer application method 400 includes various steps to form a drug-polymer coating on a stent framework.

A stent framework is cleaned, (Block 405). The stent framework may be cleaned, for example, by inserting the stent framework into various solvents, degreasers and cleansers to remove any debris, residues, or unwanted materials from the surface of the stent framework. The stent framework is dried, and generally inspected at this point in the process.

After cleaning, a primer coating may be disposed on the stent framework, particularly to metallic stent frameworks such as stainless steel, assisting in the adhesion of the laminated drug-polymer coating to the stent framework. The primer coating may include, for example, the application of a suitable primer layer such as parylene, polyurethane, phenoxy, epoxy, polyimide, polysulfone, or pellathane. The primer coating may be applied to the stent framework by dipping, spraying, painting, brushing, or other suitable methods. The primer coating is dried and cured or cross-linked as needed for eliminating or removing any volatile components. Excess liquid may be blown off prior to drying the primer coating, which may be done at room temperature or elevated temperatures under a dry nitrogen or other suitable environment including a vacuum environment.

A polymeric coating is applied onto at least a portion of the stent framework (Block 410). The polymeric coating may comprise, for example, a primer coating. The polymeric coating is applied using any suitable coating technique such as dipping, spraying, painting, or brushing. Exemplary applied polymeric coatings comprise polymers such as poly(vinyl alcohol), poly(ethylene-vinyl acetate), polyurethane, polycaprolactone, polyglycolide, poly(lactide-co-glycolide), poly(ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, and combinations thereof. Those with skill in the art will recognize that the polymeric coating may not be applied to stents composed of a polymeric base.

The dipped, sprayed or brushed stent framework is then dried (Block 415). The coated stent framework may be dried, for example, by positioning the coated stent framework in air and evaporating any solvent from the applied polymeric coating. The polymeric coating is generally dried after application by evaporating the solvent at room temperature and under ambient conditions. A nitrogen environment or other controlled environment may also be used for drying. Alternatively, the polymeric coating can be dried by evaporating the majority of any solvent at room temperature, and then further drying the coating in a vacuum environment between, for example, a room temperature of about 20 degrees centigrade and a temperature below that of the degradation temperature of the drug or polymer, for example a temperature less than 100 degrees Celsius. Drying in a vacuum environment helps to extract any pockets of solvent buried within the polymeric coating and to provide the desired level of crosslinking in the polymer.

A drug-polymeric coating is applied onto at least the drug delivery sheath (Block 420). The drug-polymer coating may also be applied to the mandrel. The polymeric coating is applied using any suitable coating technique such as dipping, spraying, painting, or brushing. Exemplary applied polymeric coatings comprise polymers such as poly(vinyl alcohol), poly(ethylene-vinyl acetate), polyurethane, polycaprolactone, polyglycolide, poly(lactide-co-glycolide), poly (ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, and combinations thereof. One or more therapeutic agents are added to and dispersed within the polymeric coating before its application onto the drug delivery sheath and/or mandrel. The therapeutic agents may be any one or more of those discussed above in relation to FIG. 1 or any other drug or therapeutic agent known in the art.

The polymer-coated stent is disposed on the drug-polymer coated mandrel so that the polymer coating on the inside diameter of the stent framework is adjacent and in contact with the drug-polymer coating of the mandrel (Block 425).

Next, the drug delivery sheath is placed on or wrapped around the stent-mandrel assembly so that the polymer coating on the outside diameter of the stent framework is adjacent and in contact with the drug-polymer coating of the drug delivery sheath (Block 430).

Once assembled, the drug or therapeutic agent coated on the sheath and or mandrel diffuses into the polymer layer coated on the stent framework (Block 435). As discussed above, the rate of diffusion may be affected by increasing the ambient temperature at which the stent/sheath assembly is placed or by increasing the pressure.

Once the drug or therapeutic agent has reached equilibrium or at a specific predetermined time, the sheath and mandrel may be removed from the stent (Block 440).

The coated stent with the drug-polymer coating may be cross-linked as needed (Block 445). Cross-linking may be done by providing additional drying cycles in air, or by heating the coated stent above a curing temperature in an oven with a controlled ambient such as vacuum, nitrogen, or air.

A delivery catheter may be coupled to the coated stent (Block 450). The delivery catheter may include an inflatable balloon that is positioned between the coated stent and the catheter and used for deploying the coated stent in the body. Alternatively, the delivery catheter may include a sheath that retracts to deploy a self-expanding version of the coated stent.

In one exemplary method, fully processed coated stents are reduced in diameter and placed into the distal end of the catheter to form an interference fit, which secures the stent onto the catheter. The catheter with the stent may be placed in a catheter package and sterilized prior to shipping and storing.

The coated stent with the drug-polymer coating may be sterilized as needed (Block 455). The stent is sterilized by any appropriate or medically conventional means. Sterilization may employ, for example, gamma-ray irradiation, e-beam radiation, ethylene oxide gas, or hydrogen peroxide gas plasma sterilization techniques. The coated stent may be packaged, shipped, and stored in a suitable package until it is used.

Figure 5:
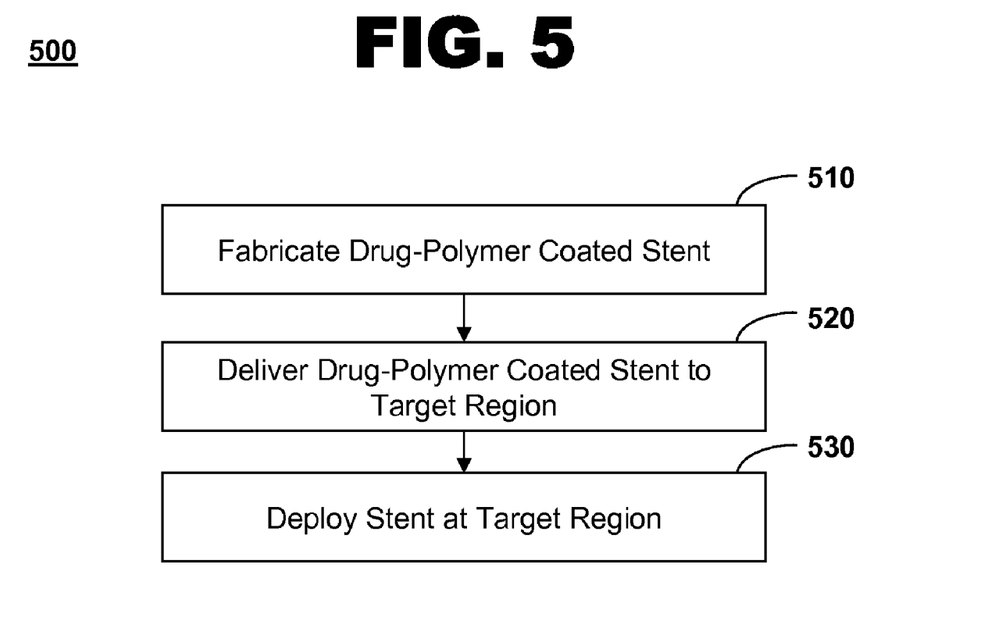
FIG. 5 is a flow diagram of a method for treating a vascular condition, in accordance with one embodiment of the current invention.

FIG. 5 shows a method of treating a vascular condition using a drug-polymer coated stent made in accordance with the present and referred to generally as method 500. Method 500 begins by fabricating a drug-polymer coated stent including at least one drug-polymer layer (Block 510). The drug-polymer coated stent may be fabricated using the method illustrated in FIG. 4.

When ready for deployment, the drug-polymer coated stent is inserted into a vessel of the body and delivered to the target region within the patient (Block 520). The stent is inserted typically in a controlled environment such as a catheter lab or hospital. The delivery catheter, which helps position the drug-polymer coated stent in a vessel of the body, is typically inserted through a small incision of the leg and into the femoral artery, and directed through the vascular system to a desired place in the vessel. Guide wires threaded through an inner lumen of the delivery catheter assist in positioning and orienting the coated stent. The position of the coated stent may be monitored, for example, with a fluoroscopic imaging system or an x-ray viewing system.

The stent is then deployed (Block 530). The stent is deployed, for example, by expanding the stent with a balloon or by extracting a sheath that allows a self-expandable stent to enlarge after positioning the stent at a desired location within the body.

Once the coated stent is deployed, the therapeutic agents in the drug-polymer coating are eluted. The elution rates of the therapeutic agents into the body and the tissue bed surrounding the stent framework are based on the polymers, thickness of the drug-polymer coating and any cap coating, and the distribution and concentration of the therapeutic agents contained therein, among other factors.

It is important to note that FIGS. 1-5 illustrate specific applications and embodiments of the present invention, and is not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

I claim:

1. A system for loading drug onto a stent, the system comprising:

a polymer coated stent;

a drug infused sheath sized to fit around the polymer coated stent; and a stent holding member including a coating on an outside surface thereof having at least one therapeutic agent contained therein, and sized to receive the polymer coated stent thereon, contact between the stent holding member and the polymer coated stent allows at least one therapeutic agent to diffuse into the polymer coating of the stent.

2. The system of claim 1, wherein the drug infused sheath comprises a flat polymer sheet having a surface coated with at least one therapeutic agent.

3. The system of claim 1 wherein the stent includes a stent framework.

4. The system of claim 3 wherein the stent framework comprises one of a metallic base or a polymeric base.

5. The system of claim 4 wherein the stent framework comprises a material selected from the group consisting of stainless steel, nitinol, tantalum, MP35N alloy, platinum, titanium, a chromium-based alloy, a suitable biocompatible alloy, a suitable biocompatible material, a biocompatible polymer, and a combination thereof.

6. A system for loading drug onto a stent, the system comprising:

a stent having a stent framework with a polymeric base;

a stent holding member sized to receive the stent; and a drug infused sheath sized to fit around the stent positioned on the stent holding member, the stent holding member including a coating on an outside surface having at least one therapeutic agent contained therein which diffuses into the stent when the stent is received thereon.

7. The system of claim 6, wherein the drug infused sheath comprises a flat polymer sheet having a surface coated with at least one therapeutic agent.

8. The system of claim 6, wherein the drug infused sheath comprises a polymeric cylinder having an inside surface, the inside surface including a drug-polymer coating applied thereon, the drug polymer coating including the at least one therapeutic agent.

9. The system of claim 6 wherein the stent framework comprises a biocompatible polymer.

* * * * *